United States Patent [19]

de Jong et al.

[11] 4,406,875

[45] Sep. 27, 1983

[54] RADIOLABELED AMINE COMPOUNDS AND THEIR USE

[75] Inventors: Rudolf B. J. de Jong, Sijbekarspel; Jan Nielsen, Schoorl, both of Netherlands

[73] Assignee: Byk-Mallinckrodt CIL B.V., Petten, Netherlands

[21] Appl. No.: 194,797

[22] PCT Filed: Feb. 7, 1980

[86] PCT No.: PCT/NL80/00005

§ 371 Date: Oct. 7, 1980

§ 102(e) Date: Oct. 7, 1980

[87] PCT Pub. No.: WO80/01685

PCT Pub. Date: Aug. 21, 1980

[30] Foreign Application Priority Data

Feb. 7, 1979 [NL] Netherlands ................ 7900964

[51] Int. Cl.³ .................... A61K 49/00; A61K 43/00
[52] U.S. Cl. ......................................... 424/1; 564/84; 564/85; 424/9
[58] Field of Search ............... 424/1, 9; 564/84, 85

[56] References Cited

U.S. PATENT DOCUMENTS

| | | | |
|---|---|---|---|
| 3,933,996 | 1/1976 | Charlton et al. | 424/1 |
| 4,024,234 | 5/1977 | Monks et al. | 424/1 |
| 4,036,945 | 7/1977 | Haber | 424/1 |
| 4,041,145 | 8/1977 | van der Veek | 424/1 |
| 4,069,254 | 1/1978 | Hidaka et al. | 260/326 S |
| 4,083,947 | 4/1978 | Monks et al. | 424/1 |
| 4,088,747 | 5/1978 | Hunt et al. | 424/1 |
| 4,091,088 | 5/1978 | Hunt et al. | 424/1 |
| 4,171,351 | 10/1979 | van der Veek | 424/1 |
| 4,250,161 | 2/1981 | de Schrijver | 424/1 |
| 4,268,495 | 5/1981 | Muxfeldt et al. | 424/1 |
| 4,292,297 | 9/1981 | Neilsen et al. | 424/1 |
| 8,812,245 | 5/1974 | Dugan | 424/1 |

FOREIGN PATENT DOCUMENTS 2081592 12/1971 France ................ 424/1

OTHER PUBLICATIONS

Hoffman et al., J. Med. Chem., vol. 18, No. 3, Mar. 1975, pp. 278–284.
Dassin et al., Biochem. Biophys. Res. Comm., vol. 91, 1979, pp. 332–337.
Dassin et al., Biochem. Biophys. Res. Comm., vol. 81, 1978, pp. 329–335.

*Primary Examiner*—Christine M. Nucker
*Attorney, Agent, or Firm*—Bernard, Rothwell & Brown

[57] ABSTRACT

Disclosed are radiolabeled amine compounds, methods for preparing these compounds, diagnostic compositions containing the radiolabeled amine compounds and methods for using these compositions in conducting radiodiagnostic examinations for determining the location and extent of an occurring blood clot in the body of a warm-blooded animal such as a human.

The radiolabeled amine compounds of the present invention have the general formula:

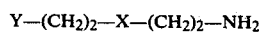

$$Y-(CH_2)_2-X-(CH_2)_2-NH_2$$

wherein X is selected from the group consisting of oxygen; sulfur; lower alkylene, radioactive selenium; and radioactive tellurium, Y is a hydrocarbyl amino group, and when X is oxygen, sulfur or lower alkylene, Y is a radioactive iodine-substituted hydrocarbyl amino group. Also disclosed are pharmaceutically-acceptable, acid addition salts of the above radiolabeled amine compounds.

28 Claims, No Drawings

RADIOLABELED AMINE COMPOUNDS AND THEIR USE

The present invention relates generally to radiolabeled amine compounds and to methods for preparing these compounds. The invention further relates to diagnostic compositions containing the radiolabeled amine compounds and to the use of these compositions in conducting radiodiagnostic examinations.

Compounds labeled with radioisotopes are useful in medical diagnostic examinations, for example, in examinations for deviations in the shape or function of internal organs. In these examinations, a composition containing the radioactive compound is administered to a patient, for example, as an injected liquid. Then, by observing the radiation emitted from the body of the patient with a suitable detection apparatus such as an external scintillation scanner or camera, an image can be obtained which indicates, for example, the organ or the pathological process in which the radioactive compound is incorporated.

For example, it is known from the article by K. A. Krohn and L. C. Knight, Seminars of Nuclear Medicine, Vol. VII, No. 3 (July 1977), p. 219-228, that fibrinogen labeled with a radioactive isotope may be useful in determining the location and extent of an occurring blood clotting process. Knowledge of the location of an occurring blood clotting process is extremely important in the clinical treatment of patients prone to undesirable blood clot formations. With sufficient knowledge of the location of occurring blood clot, successful treatment may be undertaken to counteract potential life-threatening situations caused by the occurring blood clot.

The mechanism of blood clotting or coagulation is quite complex. In accordance with fairly generally acceptable hypotheses, the normal mechanism of blood coagulation can be separated into three phases: a first phase wherein thromboplastin is formed by the interaction between certain factors in the blood, a second phase during which the prothrombin of the blood is converted to thrombin during enzymatic action of a factor activated by the thromboplastin, and a third phase in which the thrombin, a proteolytic enzyme, converts fibrinogen, a complex albumin in blood plasma, to fibrin, whereupon a solid coagulum is formed. This conversion of the fibrinogen to fibrin is believed to proceed in two steps: (1) fibrinogen, through the influence of the thrombin, loses two short chain polypeptides, and (ii) aggregation of the molecules to the positions where the two peptides were lost, to form long fibrous complexes in the form of soft aggregates, which under the influence of Factor XIII are then converted into insoluble coagulums through the formation of intermolecular amide linkages. The corpuscles of the blood then become entangled in the coagulums thereby forming a blood clot.

The initial formation of thromboplastin is activated at locations in blood vessels where damage has occurred. However, this thromboplastin, called intrinsic thromboplastin or plasma thromboplastin, can be replaced by an active product, designated extrinsic thromboplastin which is formed under the influence of a factor in the vascular tissues. The entire coagulation sequence is a series of enzymatic reactions, wherein various factors successively activate one another.

When radiolabeled fibrinogen is administered a patient for diagnostic purposes so as to determine the location of an occurring blood clotting process, the quantity of radiolabeled fibrinogen is necessarily small with respect to the large quantity of natural fibrinogen present in the circulating blood. Therefore, the quantity of radiolabeled fibrinogen which is incorporated into the fibrin network when a clot occurs is also small. As a consequence, a clot does not clearly stand out from its surroundings during an image-forming procedure in the radiodiagnostic examination.

In Rhodes et al., Radiopharmaceuticals (Soc. Nucl. Med. Inc., N.Y., N.Y. 1970) p. 521, it is suggested that radiolabeled amines might be used to label occurring blood clots. However, no specific example of any suitable radiolabeled amine was set forth in this publication.

In is therefore an object of the present invention to provide radiolabeled amine compounds which are suitable for use in radiodiagnostic examinations to determine the location and extent of an occurring blood clotting process.

In accordance with the present invention, radiolabeled amine compounds are provided which are exogenous and which during the formation of a fibrin network in an ongoing blood clotting process, are actively fixed within the network. The resulting disappearance of the radioactive amine compounds from the freely circulating blood results in a ratio between the presence of radioactivity in the clot and in the remainder of the body which is favorable for image-forming type radiodiagnostic examinations.

The radiolabeled amine compounds according to the present invention have the general formula:

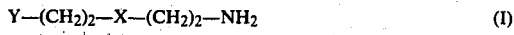

$$Y-(CH_2)_2-X-(CH_2)_2-NH_2 \qquad (I)$$

wherein X is selected from oxygen; sulfur; lower alkylene of, for example, one to about six carbon atoms such as methylene, ethylene, or trimethylene; radioactive selenium; and radioactive tellurium; and Y is a hydrocarbyl amino group; with the proviso that when X is an oxygen atom, a sulfur atom or a lower alkylene group, Y is a radioactive, iodine-substituted, hydrocarbyl amino group.

The radiolabeled amine compounds of the present invention are very suitable for use in radiodiagnostic compositions, in particular, in compositions for tracing and/or for locating blood clots or thrombi in the body of a warm blooded animal, particularly mammals such as humans.

As applied to the compounds of the present invention, the hydrocarbyl portion of the hydrocarbyl amino group is predominantly composed of carbon and hydrogen and may also include other elements such as oxygen, nitrogen or sulfur, preferably the hydrocarbyl amino group containing up to about 20 carbon atoms, most preferably from about 6 to about 16 carbon atoms. The hydrocarbyl portion of the hydrocarbyl amino group may contain aromatic or aliphatic structures or both structures such as aromatic substituted aliphatic groups which can be further substituted with other noninterfering substituents. Suitable substituents, for example, include one or more halogen atoms, i.e., chlorine, fluorine, bromine and iodine; nitro, cyano, and hydroxy groups and one or more carbon containing groups of up to about 5 or 6 carbon atoms, i.e. groups composed primarily of carbon and hydrogen and possibly nitrogen or oxygen such as alkyl, alkoxy, alkanoyl, aminoalkyl, monoalkylamino, dialkylamino, carboxy and alkoxycarbonyl. Preferably, the carbon containing groups are selected from alkyl of 1 to about 4 carbon atoms, alkoxy of 1 to about 4 carbon atoms, alkanoyl of 2 to about 5 carbon atoms, aminoalkyl of 1 to about 4 carbon atoms, mono- or dialkylamino of 1 to about 4 carbon atoms,, and alkoxycarbonyl of 2 to about 5 carbon atoms. In addition, within the scope of the present invention are salts of the above-mentioned radiolabeled amine compounds with pharmaceutically acceptable acids. Suitable acids for forming these salts include hydrochloric acid and fumaric acid.

Hydrocarbyl amino groups which contain an aromatic substituted aliphatic group as mentioned above include groups of the general formula:

$$(Ar)_n-R-\underset{|}{N}-H \qquad (II)$$

and groups of the general formula:

$$(Ar)_n-R_1-\underset{|}{N}-R_2-(Ar)_n \qquad (III)$$

where Ar is an aryl group, for example, a phenyl or naphthyl group, and may be unsubstituted or substituted, R, $R_1$ and $R_2$ may be straight or branched alkyl of one or more carbon atoms, preferably one to about four carbon atoms, n is an integer e.g. 1 to 2 and when more than 1, the rings may or may not be fused, and where the Ar, R, $R_1$ and $R_2$ groups, particularly the Ar group, may be substituted, as was mentioned above, by one or more halogen atoms, nitro, cyano, hydroxy, and/or one or more carbon containing groups of up to about 5 or 6 carbon atoms, i.e. groups composed primarily of carbon and hydrogen and, if desired, may contain nitrogen or oxygen, such as alkoxy, alkanoyl, aminoalkyl, monoalkylamino, dialkylamino, carboxy and alkoxycarbonyl. Preferably, the carbon containing groups are selected from alkyl of 1 to about 4 carbon atoms, alkoxy of 1 to about 4 carbon atoms, alkanoyl of 2 to about 5 carbon atoms, aminoalkyl of 1 to about 4 carbon atoms, monoalkylamino or dialkylamino of 1 to about 4 carbon atoms and alkoxycarbonyl of 2 to about 5 carbon atoms.

Exemplary aromatic substituted aliphatic amino groups in accordance with general formula II above, include groups containing a benzhydrylamino group. Exemplary aromatic substituted aliphatic amino groups in accordance with general formula III above, include groups containing a dibenzylamino group and a bis(phenylethyl)amino group.

Hydrocarbyl amino groups containing an arylsulfonamido group are also within the scope of the present invention and include the groups represented by the following general formula:

$$Ar-\underset{\underset{O}{\|}}{\overset{\overset{O}{\|}}{S}}-NH- \qquad (IV)$$

where Ar is an aryl group such as phenyl or naphthyl, which may be unsubstituted or substituted by, for instance, the above-mentioned substituents set forth in describing the groups of formula II and III. Exemplary arylsulfonamido groups contain benzenesulfonamido and naphthalenesulfonamido, particularly these groups substituted by one or more dialkylamino groups such as a dimethylamino group. These exemplary arylsulfonamido groups preferably are contained in compounds where X is sulfur.

The radiolabeled amine compounds of the present invention may thus include those of the general formula:

$$Y'-(CH_2)_2-X-(CH_2)_2-NH_2 \qquad (V)$$

wherein X is selected from oxygen; sulfur; lower alkylene such as methylene, ethylene, or trimethylene; radioactive selenium; and radioactive tellurium, and where, if X is radioactive selenium or tellurium, Y' is an arylamino-containing group where the arylamino portion is selected from a benzenesulfonamido-, naphthalenesulfonamidodibenzylamino,-bis-(phenylethyl)amino- and benzhydrylamino group, or where, if X is oxygen, a sulfur, or lower alkylene, Y' is a radioactive iodine-substituted arylamino containing group where the arylamino portion is selected from benzenesulfonamido- , naphthalenesulfonamido-, dibenzylamino-, bis(-phenylethyl)amino-, and benzhydrylamino- group.

Preferred radiolabeled amine compounds in accordance with the present invention have the general formula:

$$Y^1-(CH_2)_2-X'-(CH_2)_2-NH_2 \qquad (VI)$$

wherein X' is selected from oxygen, sulfur, lower alkylene such as methylene, ethylene or trimethylene, and Y' is an arylamino-containing group where the arylamino portion is selected from a benzenesulfonamido-, naphthalenesulfonamido-, dibenzylamino, bis(phenylethyl)amino or benzhydrylamino-group, the arylamino-containing group being substituted with a radioactive iodine.

Furthermore, it is within the scope of the present invention that the aryl portion, e.g. the phenyl or naphthyl radicals, of the above arylamino containing groups of the amino compounds of general formulae V and VI may be substituted with one or more substituents. Suitable substituents include one or more halogen atoms i.e., chlorine, fluorine, bromine and iodine; nitro, cyano, hydroxy and carbon containing groups of up to about 5 or 6 carbon atoms, i.e. groups composed primarily of carbon and hydrogen and, if desired, may contain, nitrogen or oxygen, examples of which include alkyl, alkoxy, alkanoyl, aminoalkyl, monoalkylamino, dialkylamino, carboxy and alkoxycarbonyl. Preferably, the carbon containing groups are selected from alkyl of 1 to about 4 carbon atoms, alkoxy of 1 to about 4 carbon atoms, alkanoyl of 2 to about 5 carbon atoms, aminoalkyl of 1 to about 4 carbon atoms, mono- or dialkylamino of 1 to about 4 carbon atoms.

Particularly preferred radiolabeled amine compounds in accordance with the present invention have the general formula:

$$Y^2-(CH_2)_2-X'-(CH_2)_2-NH_2 \qquad (VII)$$

wherein X' has the above meaning, and $Y^2$ is a radioactive, iodine-substituted benzenesulfonamido- or naphthalenesulfonamido- group which may be further substituted with one or more of the above substituents, or a salt thereof with a pharmaceutically acceptable acid.

Most preferred for the above mentioned purposes are radiolabeled amine compounds of the general formula:

$$Y^3-(CH_2)_5-NH_2 \qquad (VIII)$$

wherein $Y^3$ is a radioactive iodine-substituted naphthalenesulfonamido group or a salt thereof with a pharmaceutically acceptable acid. Examples of the above most preferred compounds include N-(5-aminopentyl)-5-iodinaphthalene-1-sulfonamide,I-131 and I-123, respectively, or the hydrochloric acid salts thereof.

As was indicated previously, the radiolabeled amine compounds in accordance with the present invention include a radioactive iodine isotope or a radioactive selenium or tellurium atom. Although various radioactive iodine isotopes may be used such as iodine-123, iodine-125, iodine-129 and iodine-131, it is presently preferred to utilize iodine-123 which has a half-life of about 13 hours, or iodine-131 which has a half-life of about eight days. Selenium-75 having a half-life of about 120 days is preferably used as the radioactive selenium atom for the purposes of the present invention. Selenium-75 can be readily prepared by neutron irradiation of enriched selenium-74 or by the bombardment of arsenic-75 with protons in a cyclotron. The tellurium-123 m isotope is the presently preferred radioactive tellurium atom for incorporation into the compounds of the present invention. The tellurium isotope can be prepared by irradiating tellurium powder in a reactor.

The radiolabeled compounds according to the present invention may generally be prepared in a manner in which is known for the synthesis of related compounds. For example, compounds of the general formula:

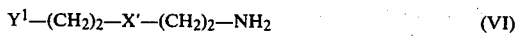
$$Y^1-(CH_2)_2-X'-(CH_2)_2-NH_2 \qquad (VI)$$

where $X'$ and $Y^1$ have the above meanings, can be prepared by reacting an alkali metal radioactive iodide with a compound of the general formula:

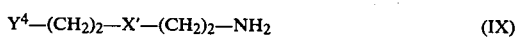
$$Y^4-(CH_2)_2-X'-(CH_2)_2-NH_2 \qquad (IX)$$

where $X'$ has the above meaning, and $Y^4$ is an iodine-substituted benzenesulfonamido-, naphthalenesulfonamido-, dibenzylamino-, bis(phenylethyl)amino-, or benzhydrylamino- group, the naphthyl or phenyl radicals of which may be substituted, in addition to iodine, with one or more of the above-mentioned substituents; or by reacting with a compound of the general formula:

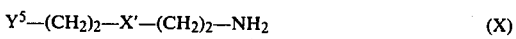
$$Y^5-(CH_2)_2-X'-(CH_2)_2-NH_2 \qquad (X)$$

where $Y^5$ is a benzenesulfonamido-, naphthalenesulfonamido-, dibenzylamino, bis(phenylethyl)amino- or benzhydrylamino- group, the naphthyl or phenyl radical of which may be substituted with one or more of the above mentioned substituents.

The reactions to produce the compounds according to the present invention may be conducted under various conditions and in various reaction media. For example, the reaction of a compound of formula IX with an alkali metal radioactive iodide may be conducted, for example, in an inert organic solvent, and, if desired, in the presence of an appropriate catalyst. Alternatively, the reaction of a compound of formula IX with an alkali metal radioactive iodide may also be conducted as a fusion reaction where the two compounds of the reaction are reacted in the absence of a solvent.

The reaction of an alkali metal radioactive iodide with a compound of formula X is an electrophilic aromatic substitution which takes place under the influence of an intermediate iodonium ion formed under reaction conditions suitable for this purpose, for example, in a polar solvent such as a mixture of methanol and water and under the influence of an oxidation agent or an iodonium ion-generating material such as, for example, N-chloro-p-toluenesulfonamide.

Methods for the preparation of compounds of formula IX and X are known in the art. For example, methods for making compounds of formula X where $Y^5$ is benzenesulfonamido- or naphthalenesulfonamido- and $X^1$ is lower alkylene of one to three carbon atoms are disclosed in U.S. Pat. No. 4,069,254 to Hidaka et al. Methods for making compounds of formula X, where X is oxygen or sulfur and $Y^5$ is naphthalenesulfonamido- are disclosed in Ljunggren et al, *J. Med. Chem.*, 1974, Vol. 17, No. 6 at p. 649. The publication by Hoffmann et al, *J. Med. Chem.*, 1975, Vol. 18, No. 3, p. 278, discloses compounds of formula X where $Y^5$ is bis(-phenylethyl) amino and $X^1$ is methylene. Other methods for making compounds of the formula X, where $X^5$ is an unsubstituted or substituted benzenesulphonamido and $X^1$ is lower alkylene can be found in U.S. Pat. No. 3,382,260 to Gruenman et al, U.S. Pat. No. 3,687,870 to Muzyczko et al, and U.S. Pat. No. 4,132,786 to Moreau et al.

Compounds of formula IX can be made by utilizing appropriate iodine substituted compounds in the above mentioned methods. For example, the patent to Hikada et al above discloses methods of making arylsulfonamidoalkylamines where the aryl portion of the compound is substituted by certain halogens. All of the abovementioned publications are incorporated herein by reference in their entirety.

The radioactive selenium or tellurium containing compounds of the present invention, i.e., the compounds of the structural formula:

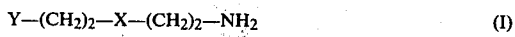
$$Y-(CH_2)_2-X-(CH_2)_2-NH_2 \qquad (I)$$

where X is radioactive Se or Te, may be prepared in generally the same manner in which the compounds of the above formula where X is a sulfur or oxygen atom can be prepared. For example, a compound of formula IV where Y is naphthalenesulfonamido and X is a radioactive tellurium atom can be prepared by reactive naphthalenesulfonyl chloride with the appropriate radioactive tellurium-containing alkylene diamine.

For diagnostic applications, the radiolabeled amine compounds according to the present invention preferably are generally formulated into compositions suitable for diagnostic purposes by incorporation with a liquid or solid pharmaceutically-acceptable carrier which is compatible with the body of the animal being diagnosed. A suitable liquid carrier is, for example, a physiological-acceptable salt solution. The amount of radiolabeled compound to be administered to the animal such as a human is that amount which will enable effective visualization of an occurring blood clot. The amount may vary with the method of administration, the particular compound used and the nature of the subject. The composition may be used as a radiodiagnostic, for example, by administration, e.g., intravenously, to an animal, in a quantity corresponding to a radioactivity of about 10 u Ci to about 25 mCi. When the animal is an adult human being, the dose administered may generally be in the range of about 0.05 mCi to about 25 mCi.

The invention will be described in greater detail with reference to the following examples. It should be understood that the examples are provided for the purpose of illustration and do not limit the invention.

EXAMPLE I

Preparation of N-(5-aminopentyl)-5-iodonaphthalene-1-sulfonamide-I-131.

An aqueous solution of carrier-free NaI (I-131) with a radioactivity of about 20 mCi was added to an ampoule containing approximately 4 mg of N-(5-aminopentyl)-5-iodonaphthalene-1-sulfonamide having a melting point of about 121°–122° C. The contents of the ampoule were lyophilized in a vacuum, after which the ampoule was sealed in a vacuum. The ampoule as a whole was then heated for about 3 hours at about 130° C. The contents of the ampoule were dissolved in about 0.3 ml of methanol and the solution was chromatographically purified over about 0.5 g. of silica gel 100 contained in a 200×3 mm column. The liquid flowing from the column was guided along a Geiger-Mueller tube in which the radioactivity of the flowing liquid was recorded by a counter and recorder. By elution with approximately 3 ml of methanol, free iodine ions were eluted; a subsequent elution was carried out with 1% acetic acid in methanol. The fraction in which radioactivity was measured was acidified with 2 N HCl and lyophilized in a vacuum. The residue was dissolved in about 15 ml. of a physiological salt solution, brought to a pH of about 5 with 0.1 N HCl, and then filtered through a 0.22 mm millipore filter.

The final product was characterized as follows:

Melting point 121° C.; no melting point depression with the starting sulfonamide.

Thin-layer chromatography with the starting materials as a reference (flux 1% acidic acid in methanol):

Final product $R_f = 0.5$
Non-reacted iodide $R_f = 0.85$.
Starting sulfonamide $R_f = 0.5$ The distribution of the radioactivity on the thin-layer plate was determined by means of a suitable measuring instrument. More than 98% of the radioactivity was found at the location of the N-(5-aminopentyl)-5-iodonaphthalene-1-sulfonamide,I-131, so at an $R_f$ value of 0.5.

EXAMPLE II

In vitro test of N-(5-aminopentyl)-5-iodonaphthalene-1-sulfonamide,I-131.

Incorporation of the radiolabeled compound produced in Example I in fibrin by means of the blood clot factor XIII was investigated in vitro in the following manner:

To about 400 ul of a physiolgical salt solution containing 10 units of Factor XIII per ml, the following solutions were successively added; (a) about 500 ul of 0.5 molar solution of cystein in a buffer solution of tris(hydroxymethyl)aminomethane having a pH of 7.4, (b) about 100 ul of a buffer solution of tris (hydroxymethyl) aminomethane having a pH of about 7.4 and in which about 250 units of thrombine per ml had been dissolved, (c) about 1200 ul of a buffer solution of tris(-hydroxymethyl) aminomethane, (d) about 50 ul of 0.4 molar solution of calcium chloride in water, and (e) about 200 ul of 5% solution of casein in water. Thereafter, about 20 ul of an aqueous solution containing the HCl salt of the above sulfonamide compound in a concentration of about 0.2 g per ml was added to the above solution to yield a final concentration of the sulfonamide compound in the total solution of about $2 \times 10^{-3}$.

In a corresponding manner, three additional test solutions were prepared in which the final concentration of the sulfonamide was about $1 \times 10^{-3}$, $5 \times 10^{-4}$ and $2.5 \times 10^{-4}$, respectively.

After incubation of the test solutions at about 37° C. for about 15 minutes, the reaction was discontinued by the addition of about 200 ul of a 1 molar solution of monoidoacetic acid which has been brought to a pH of about 7.4 by a sodium hydroxide solution. Separation of the high-molecular casein from the low-molecular weight material was then conducted by use of a column containing a molecular-sieve chromotographic medium sold under the tradename Sephadex. The radioactivity in the high-molecular fraction was then measured to determine if the radiolabeled sulfonamide compound had indeed been incorporated into the casein.

The $K_m$ value was computed from the measured radioactivity by means of a so-called "Lineweaver-Burke plot," that is, the concentration of the radiolabeled compound as a substrate in which the enzyme is occupied for 50%. A $K_m$ value of $2.5 \times 10^{-4}$ molar was determined. N-(5-aminopentyl)-5-iodonaphthalene-1-sulfonamide,I-131 thus had a smaller affinity for the enzyme than fibrin and casein, with $K_m$ values of $4 \times 10^{-5}$ and $2 \times 10^{-5}$, respectively, but amply sufficient to be incorporated efficiently in casein. Since it is generally recognized that casein and fibrin are comparable substrates, the above experiment demonstrates that the tested radiolabeled amine compound can also be incorporated efficiently in fibrin.

In summary, the result obtained by the above experiment is a clear indication that the tested radiolabeled compound can successfully be used for tracing and/or locating thrombi in the body of a warm blooded animal such as a human being.

EXAMPLE III

The radiolabeled amine compound N-(5-aminopentyl)-5-iodonaphthalenesulfonamide,I-125 is tested for its ability to be incorporated into fibrin.

The following solutions are mixed in a polystyrene test tube; (a) about 1 ml of a solution containing about 5 mg/ml of human fibrinogen (about $1.5 \times 10^{-5}$M) and a tris-HCl buffer in a concentration of about $5 \times 10^{-3}$M, the solution having a pH of about 7.4, (b) about 0.1 ml of a saline solution containing about $4 \times 10^{-2}$ units of blood Factor XIII, (c) about 0.1 ml of a 0.05 M cysteine solution having a pH of about 7.4, and (d) about 0.1 ml of a solution containing the N-(5-aminopentyl)-5-iodonaphthalenesulfonamide,I-125 compound in a concentration of about $2.3 \times 10^{-5}$ mmole and a radioactivity of about 1 $\mu$Ci. Thereafter, about 0.2 ml of solution of about 0.05 M tris buffer and about 0.025 M CaCl$_2$ which contains about 10 NIH units of human thrombin and has a pH of about 7.4 is added.

The resultant mixture is then incubated for about three and a half hours at about 37° C. whereupon a fibrin clot is formed. The clot is removed from the test tube by winding the clot about a roughened glass rod and is then washed three times in a tris buffer solution. The radioactivity of the solution and the clot are then measured in a suitable detection apparatus. From these radioactivity measurements, it is determined that about 15% of the initial radioactivity is incorporated into the fibrin clot.

EXAMPLE IV

The radiolabeled amine compound N-(5-aminopentyl)-5-iodonaphthalenesulfonamide,I-'125 is tested for stability towards deiodination and for tissue incorporation by administering the compound to rabbits.

Two test solutions each of about 0.5 mCi of the above compound (spec. activity of about 1 mCi/mg) in about 1.45 ml of a physiological saline solution are prepared. A test solution is then intravenously administered to two New Zealand white rabbits, each weighing about 3 kg.

A blood sample is then taken from each rabbit at 12, 24, 36 and 72 hour periods after administration. The radioactivity of about 1 g of blood from samples for each time period is then measured. The measurements indicate that the radioactivity in the blood decreases slowly and that at about 72 hours after administration, about 20% of the initial radioactivity is still present in the blood. Due to the relatively slow disappearance of the subject compound from the bloodstream, the compound is therefore available in the bloodstream for a prolonged period of time which thereby increases its suitability to become incorporated into an occurring thrombus.

At the end of the 72 hour period, the rabbits are sacrificed and thereafter, the thyroid, liver, kidneys, lung, stomach wall, parotid glands, brains, muscle and bone tissue are removed and portions are measured for radioactivity. The thyroid contains only about 0.05% of the injected dose per gram which thereby indicates the stability of the subject compound towards deiodination. In addition, the stomach wall tissue and the parotid glands show a similar low uptake of iodine. The liver contains about 0.04% and the gall bladder contains about 0.1% of the injected dose while the kidneys and the urine both contain about 0.3% of the dose. Hence it may be concluded that the primary manner of excretion of the compound is via the kidneys.

EXAMPLE V

The radiolabeled amine compound N-(5-amino-3-thiapentyl)-5-iodonaphthalene-1-sulfonamide,I-131 is prepared.

In preparing the subject compound, a solution of 5-iodonaphthalenesulfochloride in methylene chloride is added dropwise to a solution of bis- (2-aminoethyl) sulfide and triethylamine in a molar ratio of about 1:2 in methylene chloride and then allowed to form the reaction product N-(5-amino-3-thiapentyl)-5-iodonaphthalene-1-sulfonamide. After washing with a sodium bicarbonate solution, the reaction product is crystallized by concentrating the methylene chloride solution and the addition of $CCl_4$.

About 3 mg of the reaction product is then weighed into a glass ampoule. Thereafter, about 10 mCi of sodium iodide, I-131 which is suitable for iodination of peptides is added. The solvent is evaporated in vacuum under the necessary safety precautions. To the resultant dry mass is added about 0.2 ml xylene which contains about 1 mg of dibenzo(18)crown-6. The ampoule is sealed in vacuo and is then heated for about 3 hours at about 130° C. The contents of the ampoule are purified over a column of about 0.5 g Bio-Rex 70,H+ form, exchange material by first washing out the unreacted NaI, I-131 with methanol. The radiolabeled compound is eluted from the column with about 1 ml of about 0.1 N HCl in methanol. The eluate is neutralized with about 0.1 N NaOH and evaporated to dryness in a vacuum. The residue is taken up in a saline solution to yield a solution of the above radiolabeled amine compound.

EXAMPLE VI

The radiolabeled amine compound N-(5-amino-3-selenapentyl)-naphthalene-1-sulfonamide, Se-75 is prepared.

To an ice cold solution of about 0.5 mmole of naphtalene-1-sulfochloride in methanol which contains about 3 mmoles of triethylamine, a solution of 0.5 mmole of 2-bromoethylammoniumbromide in methanol is slowly added. When the addition is completed, stirring is continued for about one hour at ambient temperature. The reaction liquor is washed with a 5% sodium bicarbonate solution and then dried on molecular sieves thereby yielding N-(2-bromoethyl)naphthalene-1-sulfonamide.

Se powder enriched in Se-74 is irradiated in a nuclear reactor with a neutron flux of about $3.10^{14}$ n.sec.$^{-1}$—cm$^{-2}$ to a specific activity of about 1 Ci/mmole. Thereafter, about 0.5 mmole of the radioactive selenium is reacted with about 1 mmole $NaBH_4$ in ethanol to yield sodium hydrogenselenide, Se-75.

All of the following steps are conducted in a nitrogen atmosphere where the presence of oxygen is strictly excluded. In this atmosphere, a 0.5 mmole solution of 2-bromoethylammoniumbromide in absolute methanol is cooled to about −30° C. and then 0.5 mmole of sodium methoxide in methanol is added under vigorous stirring. The cold mixture is added slowly to the above sodium hydrogenselenide solution while the reaction temperature is maintained at about 0° C. When the addition is complete, another 0.5 mmole of sodium methoxide in methanol is added and the temperature slowly raised to about ambient temperature. Stirring is continued for about one hour, whereafter the temperature is raised to about 40° C. and the mixture maintained at this temperature for about one hour and then cooled. The reaction mixture contains sodium-2-aminoethylselenide, Se-75.

The N-(2-bromoethyl)naphthalene-1-sulfonamide prepared previously is filtered from the molecular sieves and immediately added to the reaction mixture containing the sodium-2-aminoethylselenide, Se-75. The resultant mixture is stirred for about two hours at ambient temperature and then for about two hours at about 40° C. The solvent was distilled off in vacuo and the residue dissolved in methylene chloride. The solution is washed with water and the methylene chloride solution filtered through phase-separating filter paper. The solvent is evaporated in vacuo and the residue dissolved in methanol. The methanol solution is then passed over a column of Bio-Rad 50W-X-8 ion exchange material and nonionic compounds are washed from the column with 50% solution of methanol in water. The subject N-(5-amino-3-selenapentyl)naphthalene-1-sulfonamide, Se-75 compound is eluted from the column with 0.5 N HCl in 50% methanol.

EXAMPLE VII

The radiolabeled amine compound N-(bis-(4-iodobenzyl)-1,5-diaminopentane,I-131 is prepared.

Equimolar amounts of bis-(4-iodobenzyl)amine. N-(5-bromopentyl)phthalimide and triethylamine in a dry diethoxyethane solvent are heated at reflux and in a nitrogen atmosphere for about three hours. The solvent is evaporated in vacuo, the residue dissolved in water and then the residue is extracted with methylene chloride. The methylene chloride solution is filtered through phase-separating paper and purification is effected by chromatography on silica gel to yield the essentially pure compound N-(bis-(4-iodobenzyl)-1,5-diaminopentane.

The purified compound is then refluxed with an equimolar amount of hydrazine hydrate in absolute ethanol for about two hours. The resultant reaction mixture is cooled to 0° C. and 36% HCl is added. The mixture is stirred for about 15 minutes at about 0° C. and is then filtered. The residue is washed quickly with cold ethanol and the combined washings and filtrate are concentrated in vacuo. The concentrated solution is then made alkaline with the addition of a 4N NaOH solution and extracted with ether. The ether extract is dried and HCl gas is passed through the solution to yield the HCl salt of the above diaminopentane compound. The free amine form is obtained by dissolution of the HCl salt in methanol, adding the ion exchange material Bio-Rad AG 1-X-8 and then filtering off the ion exchange material after a period of time.

Sufficient solution of the N-(bis-(4-iodobenzyl)-1,5-diaminopentane compound to provide about 5 mg of the compound is then added to a glass ampoule. Thereafter, about 10 mCi of a solution of NaI, I-131 is added and the contents of the ampoule dried in vacuo under the necessary precautions to entrap any I-131 that is volatilized. The ampoule is sealed in vacuo and is then heated at about 140° for about three hours. The contents of the ampoule are dissolved in a small amount of methanol and poured onto a column of about 0.5 g Bio-Rex 70 exchange material within a disposable syringe. Ionic iodide is washed from the column with about 2 ml of methanol and the N-(bis-(4-iodobenzyl)-1,5-diaminopentane,I-131 compound is then eluted from the column with 0.1 N HCl in methanol.

While the present invention has been described with reference to particular embodiments thereof, it will be understood that numerous modifications may be made without departing from the spirit and scope of the invention.

What is claimed is:

1. A radiolabeled amine compound of the general formula:

$$Y-(CH_2)_2-X-(CH_2)_2-NH_2$$

wherein X is selected from the group consisting of oxygen; sulfur; lower alkylene; radioactive selenium; and radioactive tellurium; and when X is a radioactive selenium or tellurium atom, Y is a hydrocarbyl amino group, and when X is an oxygen atom, a sulfur atom or a lower alkylene group, Y is a radioactive iodine-substituted hydrocarbyl amino group; or a pharmaceutically acceptable acid salt of said amine compound.

2. A radiolabeled amine compound in accordance with claim 1 wherein X is lower alkylene containing 1 to about 6 carbon atoms.

3. A radiolabeled amine compound in accordance with claim 2 wherein the lower alkylene group is selected from the group consisting of methylene, ethylene and trimethylene.

4. A radiolabeled amine compound in accordance with claim 1 wherein the hydrocarbyl amino group comprises an aromatic-substituted, aliphatic group.

5. A radiolabeled amine compound in accordance with claim 4 wherein the hydrocarbyl amino group has the general formula:

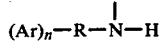

or the general formula:

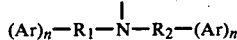

where Ar comprises an aryl group, R, R₁ and R₂ are straight or branched alkyl and n is an integer from 1 to 2.

6. A radiolabeled amine compound in accordance with claim 1 wherein the hydrocarbyl amino group comprises an arylsulfonamido group.

7. A radiolabeled amine compound in accordance with claim 6 wherein the arylsulfonamido group has the general formula:

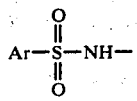

where Ar comprises aryl group selected from phenyl and naphthyl.

8. A radiolabeled amine compound in accordance with claim 7 wherein Ar is substituted with a dimethylamino group.

9. A radiolabeled amine compound in accordance with claims 4, 5 or 6 wherein X is lower alkylene containing 1 to about 6 carbon atoms.

10. A radiolabeled amine compound in accordance with claim 9 wherein the lower alkylene group is selected from the group consisting of methylene, ethylene and trimethylene.

11. A radiolabeled amine compound of the general formula:

$$Y-(CH_2)_2-X-(CH_2)_2-NH_2$$

wherein X is selected from the group consisting of oxygen, sulfur, lower alkylene, radioactive selenium and radioactive tellurium, and where, if X is radioactive selenium or tellurium, Y is an arylamino group selected from the group consisting of a benzenesulfonamido-, naphthalenesulfonamido-, dibenzylamino-, bis(phenylethyl)amino- and benzyhdrylamino group, or where, if X is oxygen, sulphur, or lower alkylene, Y is a radioactive iodine-substituted arylamino group selected from benzenesulfonamido-, naphthalenesulfonamido-, dibenzylamino-, bis(phenylethyl)amino- and benzhydrylamino-; or a pharmaceutically-acceptable, acid salt of said amine compound.

12. A radiolabeled amine compound in accordance with claim 11 wherein the arylamino group is substituted by one or more substituent groups selected from the group consisting of halogen, nitro, cyano, hydroxy and carbon containing groups of up to about 6 carbon atoms.

13. A radiolabeled amine compound in accordance with claim 12 wherein the substituent group is a carbon-containing group selected from the group consisting of alkyl, alkoxy, alkanoyl, aminoalkyl, monoalkylamino, dialkylamino, carboxy and alkoxycarbonyl.

14. A radiolabeled amine compound in accordance with claim 11 wherein X is selected from oxygen, sulphur, lower alkylene and Y is an arylamino selected from a benzenesulfonamido-, naphthalenesulfonamido-, dibenzylamino, bis(phenylethyl)amino or benzhydrylamino- group which is substituted with radioactive iodine.

15. A radiolabeled amine compound in accordance with claim 14 wherein X is lower alkylene selected from the group consisting of methylene, ethylene and trimethylene.

16. A radiolabeled amine compound in accordance with claim 14 wherein Y is selected from the group consisting of a radioactive iodine-substituted benzenesulfonamido- and a radioactive iodine substituted naphthalenesulfonamido- group.

17. A radiolabeled amine compound in accordance with claim 16 wherein X is lower alkylene selected from the group consisting of methylene, ethylene and trimethylene.

18. A radiolabeled amine compound in accordance with claim 16 wherein X is methylene and Y is a radioactive iodine-substituted naphthalenesulfonamido group.

19. N-(5-aminopentyl)-5-iodonaphthalene-1-sulfonamide-I-131 or a pharmaceutically-acceptable, acid salt thereof.

20. N-(5-aminopentyl)-5-iodonaphthalene-1-sulfonamide-I-123 or a pharmaceutically-acceptable, acid salt thereof.

21. A radiodiagnostic composition adapted for use in tracing and/or locating thrombi in a warm-blooded animal wherein said composition comprises the radiolabeled amine compound in accordance with claims 1, 3, 5, 8, 11, 14, 16, 17, 18, 19 or 20 and a pharmaceutically-acceptable carrier material.

22. A method for conducting a radiodiagnostic examination for tracing and/or locating thrombi in the body of an animal wherein said method comprises administering to the animal a radiodiagnostic composition containing the radiolabeled amine compound in accordance with 1, 3, 5, 8, 11, 14, 16, 17, 18, 19, or 20 and a pharmaceutically acceptable carrier material, the quantity of radiodiagnostic composition administered having a radioactivity of about 10 uCi to about 25 mCi.

23. A method for preparing a radiolabeled amine compound useful in radiodiagnostic examinations wherein said method comprises reacting an alkali metal radioactive iodide with a compound of the general formula:

$$Y-(CH_2)_2-X-(CH_2)_2-NH_2$$

characterized in that X is selected from the group consisting of oxygen, sulfur, and lower alkylene, Y is a arylamino group selected from the group consisting of benzene sulfonamido-, naphthalenesulfonamido-, dibenzylamino-, bis(phenylethyl)amino- and benzhydrylamino-.

24. A process in accordance with claim 23 wherein the arylamino group is substituted by a substituent group selected from the group consisting of halogen, nitro, cyano, hydroxy and carbon containing groups of up to about 6 carbon atoms.

25. A process in accordance with claim 24 wherein the substituent groups include iodine.

26. A process in accordance with claim 23 where the iodide is reacted with the compound in an inert organic solvent.

27. A radiolabeled amine compound in accordance with claim 12 wherein X is selected from oxygen, sulphur, lower alkylene and Y is an arylamino selected from a benzenesulfonalmido-, naphthalenesulfonamido-, dibenzylamino, bis(phenylethyl)amino or benzhydrylamino- group which is substituted with radioactive iodine.

28. A radiolabeled amine compound in accordance with claim 13 wherein X is selected from oxygen, sulphur, lower alkylene and Y is an arylamino selected from a benzenesulfonamido-, naphthalenesulfonamido-, dibenzylamino, bis(phenylethyl)amino or benzhydrylamino- group which is substituted with radioactive iodine.

* * * * *

UNITED STATES PATENT AND TRADEMARK OFFICE
CERTIFICATE OF CORRECTION

PATENT NO. : 4,406,875

DATED : September 27, 1983

INVENTOR(S) : de Jong et al.

It is certified that error appears in the above-identified patent and that said Letters Patent is hereby corrected as shown below:

Column 14, claim 23, the formula beginning on line 8 should be on one line as:

"$Y - (CH_2)_2 - X - (CH_2)_2 - NH_2$"

Signed and Sealed this

Thirty-first Day of January 1984

[SEAL]

Attest:

GERALD J. MOSSINGHOFF

Attesting Officer

Commissioner of Patents and Trademarks